US006740317B1

(12) United States Patent
Cho et al.

(10) Patent No.: US 6,740,317 B1
(45) Date of Patent: May 25, 2004

(54) HAIR CARE COMPOSITIONS AND IMPROVED HAIR QUALITY

(75) Inventors: Suk H. Cho, Idaho Falls, ID (US); Becky Zehntner, Blackfoot, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 09/753,906

(22) Filed: Jan. 3, 2001

(51) Int. Cl.$^7$ .................................................. A61K 7/06
(52) U.S. Cl. ........................................................ 424/70.1
(58) Field of Search .............................. 424/43, 45, 47, 424/70.1, 70.4, 70.19

(56) References Cited

U.S. PATENT DOCUMENTS

| | | | |
|---|---|---|---|
| 2,798,053 A | | 7/1957 | Brown |
| 5,476,649 A | | 12/1995 | Naito et al. |
| 5,502,226 A | | 3/1996 | Cho et al. |
| 5,540,853 A | * | 7/1996 | Trinh et al. |
| 5,698,828 A | | 12/1997 | Perkins |
| 5,905,165 A | | 5/1999 | Mahieu et al. |
| 5,976,516 A | | 11/1999 | Sakai et al. |
| 6,103,679 A | * | 8/2000 | Van der Weerdt et al. |

FOREIGN PATENT DOCUMENTS

| | | |
|---|---|---|
| FR | 2273492 | 2/1976 |
| JP | 52102288 A2 | 8/1977 |
| JP | 7247279 A2 | 9/1995 |
| RO | 113142 | 4/1998 |

OTHER PUBLICATIONS

Robbins, Clarence R., *Chemical and Physical Behavior of Human Hair*, Ch. 8, "The Physical Properties and Cosmetic Behavior of Hair", 35 pages (1979).
Robbins, *Chemical and Physical Behavior of Human Hair*, (1994) 3$^{rd}$ Edition, Springer–Verlag.
Singleton, et al., *Am. J. Enol. Vitic.*, (1965) 16:144–158.

* cited by examiner

*Primary Examiner*—Thurman K. Page
*Assistant Examiner*—Robert M Joynes
(74) *Attorney, Agent, or Firm*—Fish & Richardson P.C.P.A.

(57) ABSTRACT

The invention provides methods and materials for improving or maintaining hair care. Such hair care compositions can contain a macrocyclic lactone and/or an eicosanoate ester. In addition, the hair care compositions can contain a grape skin extract, a benzophenone, and/or an aryl benzotriazole. Further, the hair care methods and materials can provide increased hair manageability as well as protection against sun exposure (e.g., exposure to ultraviolet radiation) and repeated chemical treatment.

24 Claims, No Drawings

HAIR CARE COMPOSITIONS AND IMPROVED HAIR QUALITY

BACKGROUND

1. Technical Field

The invention relates to hair care and hair care compositions. Specifically, the invention relates to hair care compositions that provide increased hair manageability as well as improved styling and conditioning abilities.

2. Background Information

Many different hair care products are used to treat hair. For example, shampoos are used to clear hair, while styling gels are used to increase hair manageability. Not all hair care product, however, result in healthy hair. For example, some hair care products can remove natural components from hair causing damage. In addition, hair treatments such as dyeing, relaxing, or permanent waving can damage hair. Hair also can be damaged or weakened by the action of mechanical, atmospheric, and/or chemical exposure. For example, radicals from ultraviolet radiation and the peroxide treatment step of dying hair can cause damages that result in weakened, dry, and brittle hair. The most apparent effect is the bleached appearance of hair after exposure to intense sunlight during the summer months. Hair also can suffer abrasion damage caused by a multitude of factors such as grooming, combing, blow-drying, and curling.

SUMMARY

The invention involves hair care and hair care compositions. Specifically, the invention provides methods and materials for improving or maintaining hair care. The hair care compositions provided herein can contain a macrocylic lactone and/or an eicosanoate ester. In addition, the hair care compositions provided herein can contain a grape skin extract, a benzophenone, and/or an aryl benzotriazole.

The hair care compositions provided herein can (1) impart hair with suppleness, (2) improve the feel of hair, and (3) decrease hair damage. For example, the hair care compositions within the scope of the invention can reduce hair damage caused by abrasion. The hair care compositions provided herein also can provide hair having an improved conditioning feel. For example, hair treated with the compositions provided herein can have a moisturized feeling that is evident by finger or comb-passing ease as well as styling ease. In addition, the hair care compositions within the scope of the invention can provide protection against sun exposure (e.g., exposure to ultraviolet radiation) and repeated chemical treatment. Moreover, the hair care compositions provided herein can be aqueous hair care compositions with superior rheological stability and aesthetic properties.

The methods provided herein can be used to clean, condition, or style hair while providing radical scavenging protection from sun exposure and/or chemical treatment. In addition, the methods provided herein can be used to treat hair such that macrocylic lactone and/or eicosanoate ester molecules bind to hair fibers providing the hair with a lustrous, healthy, moisturized, and youthful impression that can be obtained for long periods of time.

In general, the invention features an aqueous hair care composition containing a macrocyclic lactone. The composition can be a shampoo, conditioner, styling gel, styling spray, or styling non-aerosol mousse. The macrocyclic lactone can be, by weight, from about 0.001 percent to about 10.0 percent of the composition. The macrocyclic lactone can be hexadecanolide. The composition can contain an eicosanoate ester. The eicosanoate ester can be a branched eicosanoate ester or a straight eicosanoate ester. The eicosanoate ester can be methyl 11-cis eicosenaote, 18-methyl eicosanaote, or a quaternary ester of 18-methyl eicosanaote. The eicosanoate ester can be, by weight, from about 0.001 percent to about 10.0 percent of the composition. The composition can contain a conditioning polymer. The conditioning polymer can be a cationic conditioning polymer. The conditioning polymer can be, by weight, from about 0.001 percent to about 10.0 percent of the composition. The composition can contain silicone. The silicone can be, by weight, from about 0.001 percent to about 10.0 percent of the composition. The silicone can be, by weight, from about 0.05 percent to about 2.5 percent of the composition. The viscosity of the silicone can be from about 50 cst to about 2,000,000 cst at 25° C. The viscosity of the silicone can be from about 150 cst to about 1,000,000 cst at 25° C. The composition can contain a surfactant. The surfactant can be, by weight, from about 0.001 percent to about 10.0 percent of the composition. The surfactant can be an anionic surfactant, cationic surfactant, or nonionic surfactant. The composition can contain a thickener. The pH of the composition can be from about 4.0 to about 8.5. The composition can contain an eicosanoate ester, a conditioning polymer, and silicone. The composition can contain (a) an eicosanoate ester, the eicosanoate ester being from about 0.001 percent to about 10.0 percent of the composition; (b) a conditioning polymer, the conditioning polymer being from about 0.001 percent to about 10.0 percent of the composition; and (c) silicone, the silicone being from about 0.001 percent to about 10.0 percent of the composition.

In another embodiment, the invention features an aqueous hair care composition containing an eicosanoate ester. The composition can be a shampoo, conditioner, styling gel, styling spray, or styling non-aerosol mousse. The eicosanoate ester can be, by weight, from about 0.001 percent to about 10.0 percent of the composition. The composition can contain a macrocyclic lactone. The macrocyclic lactone can be, by weight, from about 0.001 percent to about 10.0 percent of the composition. The composition can contain a conditioning polymer, silicone, surfactant, and a thickener. It is noted that the composition can contain any of the ingredients or characteristics described herein. For example, the composition can contain a fragrance.

Another embodiment of the invention features a method of treating hair. The method includes applying a composition containing a macrocyclic lactone to the hair. It is noted that the composition can contain any of the ingredients or characteristics described herein. For example, the composition can contain a fragrance.

Another embodiment of the invention features a method of treating hair. The method includes (a) applying a composition containing a macrocyclic lactone to the hair, and (b) heating the hair to at least 75° C. It is noted that the composition can contain any of the ingredients or characteristics described herein. For example, the composition can contain a fragrance.

Another embodiment of the invention features a method of treating hair. The method includes applying a composition containing an eicosanoate ester to the hair. It is noted that the composition can contain any of the ingredients or characteristics described herein. For example, the composition can contain a fragrance.

Another embodiment of the invention features a method of treating hair. The method includes (a) applying a composition containing an eicosanoate ester to the hair, and (b) heating the hair to at least 75° C. It is noted that the composition can contain any of the ingredients or characteristics described herein. For example, the composition can contain a fragrance.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides methods and materials related to hair care. Specifically, the invention provides methods and materials that are used to impart hair with suppleness, improve the feel of hair, and decrease hair damage. In addition, the invention provides methods and materials that are used to protect hair against sun exposure (e.g., exposure to ultraviolet radiation) and repeated chemical treatment. The term "hair care composition" as described herein refers to any product that can be used to clean or treat hair. Such hair care compositions include, without limitation, shampoos, conditioners, styling gels, styling sprays, and styling non-aerosol mousse. The term "hair" as used herein refers to all hair including, without limitation, head hair, eyelashes, mustaches, beards, and body hair. The hair care compositions described herein can contain any of the following ingredients. For example, a hair care composition within the scope of the invention can contain a macrocylic lactone or an eicosanoate ester. In addition, the hair care compositions described herein can contain any combination of the following ingredients. For example, a hair care composition within the scope of the invention can contain a macrocyclic lactone, an eicosanoate ester, a grape skin extract, a benzophenone, and a benzotriazole.

Macrocyclic Lactone

In one embodiment, the invention provides hair care compositions that contain one or more macrocyclic lactones. A macrocyclic lactone refers to any compound having the following structure:

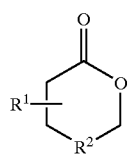

where $R^1$ is a hydroxyl, hydrogen, methyl, or ethyl group, and $R^2$ is a straight or branched alkyl or alkenyl radical group having 8 to 24 carbon atoms. Examples of macrocyclic lactones include, without limitation, heptadecanolide, hexadecanolide, tetradecanolide, octadecanolide, 2-hydroxy-hexadecanolide, docosanolide, and eicosanolide. Any method can be used to obtain a macrocyclic lactone. For example, a macrocyclic lactone can be obtained using any of the methods described in U.S. Pat. No. 5,502,226; Japanese Patent No. 07247279 A2; and Japanese Patent No. 52102288 A2. In addition, a macrocyclic lactone can be obtained from IFF (New York, N.Y.) and Sigma (St. Louis, Mo.).

The hair care compositions described herein can contain any amount of a macrocyclic lactone. For example, a hair care composition can contain an effective amount of macrocyclic lactone such that the hair care composition provides a sufficient level of manageability to hair. Typically, from about 0.001 percent to about 10 percent (e.g., from about 0.005 percent to about 8 percent or from about 0.01 percent to about 5 percent), by weight, of the hair care composition is a macrocyclic lactone.

Eicosanoate Ester

In another embodiment, the invention provides hair care compositions that contain one or more eicosanoate esters. The eicosanoate ester can be a straight eicosanoate ester or a branched eicosanoate ester. An eicosanoate ester refers to any compound having the following structure:

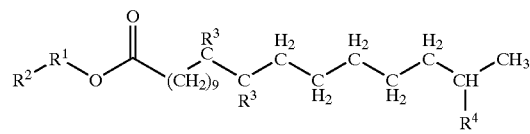

where $R^1$ is an alkyl ester containing an alkyl group of from 1 to 5 carbons; $R^2$ is a hydrogen, alkyl, hydroxyl, or quaternary ammonium radical group; $R^3$ is a hydrogen or methyl group where the bond between the two $CR^3$ groups is saturated or unsaturated; and $R^4$ is a hydrogen, alkyl, or alkenyl group. Examples of eicosanoate esters include, without limitation, methyl eicosanoate, ethyl eicosanoate, methyl 18-methyl eicosanoate, methyl 11-cis eicosenoate, trimethylammoniumethyl eicosanoate, methyl 11-trans eicosenoate, hydroxyethyl 18-methyleicosanoate, trimethylammoniumethyl 18-methyleicosanoate, and trimethylammoniumpropyl 18-methyleicosanoate. Any method can be used to obtain an eicosanoate ester.

The hair care compositions described herein can contain any amount of an eicosanoate ester. For example, a hair care composition can contain an effective amount of eicosanoate ester such that the hair care composition provides a sufficient level of manageability to hair. Typically, from about 0.001 percent to about 10 percent (e.g., from about 0.01 percent to about 8 percent or from about 0.05 percent to about 5 percent), by weight, of the hair care composition is an eicosanoate ester.

Grape Skin Extract

In another embodiment, the invention provides hair care compositions that contain one or more grape skin extracts. A grape skin extract can be an aqueous grape skin extract, a hydroalcoholic grape skin extract, or an aqueous grape skin extract powder. Any grape skin extract can be used. For example, grape skin extracts from red or white grapes can be used. Examples of grapes that can be used to make a grape skin extract include, without limitation, White Zinfandel, Chardonnay, Ruby Red, French Combard, and Cabernet-Sauvignon grapes. The hair care compositions within the scope of the invention can contain a single type of grape skin extract (e.g., Ruby Red grape skin extract) or a mixture of different grape skin extracts (e.g., White Zinfandel grape skin extract and Ruby Red grape skin extract).

A grape skin extract can be made using any extraction method. For example, a grape skin extract can be produced by extracting grape skin and seed pomace with an aqueous medium. The aqueous extract then can be adsorbed in an organic column. Once adsorbed, the extract can be desorbed with alcohol (e.g., ethanol). The collected eluent can be spray dried. Alternatively, grape skin extracts can be obtained commercially from, for example, Polyphenolics Inc. (Burlingame, Calif.) and Bio Serae Laboratories SA (Montolieu, France).

The hair care compositions described herein can contain any amount of grape skin extract. For example, a hair care composition can contain an effective amount of grape skin extract such that the hair care composition provides protection against ultraviolet radiation or chemical treatment. Alternatively, a hair care composition can contain an effective amount of grape skin extract in combination with aryl benzotriazole and benzophenone such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is grape skin extract.

The hair care compositions described herein can contain a grape skin extract that is water dispersible and/or a soluble powder derived from aqueous extraction. A grape skin extract can be standardized for total phenols based on an analysis described by Singleton el al. (Am. J. Enol. Vitic, 16, 144–158 (1965)). Typically, a grape skin extract used in a hair composition described herein has total phenolics from about 15 percent to about 100 percent (e.g., from about 20 percent to about 95 percent or from about 25 percent to about 85 percent). In addition, a grape skin extract used in a hair composition described herein contains an effective amount of anthocyanin. For example, from about 0.01 percent to about 50 percent (e.g., from about 0.05 percent to about 45 percent, or from about 0.1 percent to about 40 percent) of a grape skin extract can be anthocyanin.

Benzophenone

In another embodiment, the invention provides a hair care composition that contains one or more benzophenone. A benzophenone refers to any compound having the following structure:

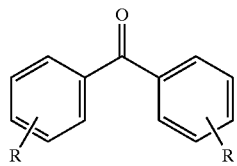

where each R can independently be a hydroxy, alkyl, alkoxy, sulfonate, phosphate, or carboxylate. For example, one R can be a hydroxy group while the other R is a carboxylate group.

A hair care composition can contain a benzophenone that has compatible physicochemical properties such that the benzophenone is dispersible and/or soluble in an aqueous media. Examples include, without limitation, those benzophenones having sulfonate, multi-hydroxy, dimethoxy sulfonyl, and/or carboxylates as the R groups. For example, a hair care composition within the scope of the invention can contain benzophenone-2, benzophenone-3, benzophenone-4, and/or benzophenone-9.

The hair care compositions described herein can contain any amount of a benzophenone. For example, a hair care composition can contain an effective amount of a benzophenone such that the hair care composition provides protection against ultraviolet radiation or chemical treatment. Alternatively, a hair care composition can contain an effective amount of a benzophenone in combination with aryl benzotriazole and a grape skin extract such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is a benzophenone.

Any method can be used to obtain a benzophenone. For example, a benzophenone can be obtained from ISP (Wayne, N.J.), Rhone-Poulenc (Cranbury, N.J.), or BASF (Mount Olive, N.J.).

Benzotriazole

In another embodiment, the invention provides a hair care composition that contains one or more benzotriazole. A benzotriazole refers to any compound having the following structure:

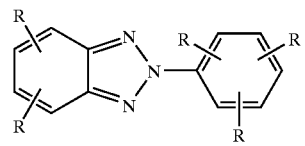

where each R can independently be a hydrogen, a straight alkyl or alkenyl radical group, a branched alkyl or alkenyl radical group, hydroxyl, sulonfate, phosphate, sulfate, alkoxy, carboxylate, or nitro group. For example, one R can be a carboxylate group while the four other R groups are hydrogens.

A hair care composition can contain a benzotriazole that is dispersible and/or soluble in an aqueous media. Examples include, without limitation, those benzotriazoles containing a water-soluble functionality as sulfonates, sulfates, or phosphates with 1 to 3 hydroxyl groups. For example, a hair care composition within the scope of the invention can contain sodium-3-(2H-benzotriazole-2-yl)-5-sec-butyl-4-hydroxybenzenesulfonate, sodium-3-(2H-benzotriazole-2-yl)-5-propyl-4-hydroxybenznesulfate; potassium-3-(2H-benzotriazole-2-yl)-5-sec-hexyl-4-hydroxybenzenephosphate, ammonium-3-(2H-benzotriazole-2-yl)-5-sec-butyl-4-hydroxybenzenesulfonate, sodium-3-(2H-benzotriazole-2-yl)-5-ethyl-4-hydroxybenznesulfonate, sodium-3-(2H-benzotriazole-2-yl)-5-sec-butyl-4-hydroxybenzenesulfonate, or sodium-3-(2H-benzotriazole-2-yl)-5-sec-butylbenzne-di-sulfonate.

The hair care compositions described herein can contain any amount of a benzotriazole. For example, a hair care composition can contain an effective amount of a benzotriazole such that the hair care composition provides protection against ultraviolet radiation or chemical treatment. Alternatively, a hair care composition can contain an effective amount of a benzotriazole in combination with benzophenone and a grape skin extract such that the hair care composition provides protection against ultraviolet radiation or chemical treatment. Typically, from about 0.001 percent to about 10 percent (e.g., from about 0.01 percent to about 8 percent or from about 0.05 percent to about 5 percent), by weight, of the hair care composition is a benzotriazole.

Any method can be used to obtain a benzotriazole. For example, a benzotriazole can be obtained from Ciba Specialty Chemicals (High Point, N.C.).

Film Forming Polymers

The hair care compositions of the invention can contain one or more film forming polymers. A film forming polymer can be used to adhere a UV protector (e.g., grape skin extract, benzophenone, or benzotriazole) to hair. In addition, film forming polymers can be used to improve substantivity and hair styling. Any type of film forming polymer can be used. For example, a film forming polymer can be made of monomers such as acrylic acid, methacrylic acid, N,N-dimethylaminoethylmethacrylate, N,N-dimethylacrylamide, N-t-butyl acrylamide, vinyl acetate, vinyl pyrrolidone, crotonic acid, itaconic acid, octylacrylamide, butylaminoethyl methacrylate, vinyl neodecanoate, styrene sulfonate, hydroxyethylmethacrylate, vinyl ether and ethylene, hydroxy cellulose, chitosan, propylene and methoxyethyl methacrylate, or mixtures thereof. A film forming polymer can be a homopolymer or copolymer. Examples of film forming polymers include, without limitation, polyvinly pyrrolidone, polyvinyl alcohol, vinyl pyrroloidone/dimethylamino propyl acrylamide copolymer, deacetylated chitosan, octylacrylamide/acrylate/butylaminoethyl methacrylate copolymer, vinylacetate/crotonates/vinyl neodecanoate copolymer, polyacrylate, polymethacrylate, acrylate/methacrylate copolymer, hydroxyethylamethacrylate/dimethylaminoethylmethacrylate/methacrylic acid copolymer, acrylate/octylacrylamide copolymer, and octylacrylamide/acrylate/butylaminoethyl methacrylate copolymer. The film forming polymer can have a glass transition temperature from about −20° C. to about 150° C. (e.g., from about −10° C. to about 100° C. or from about 0° C. to about 80° C.).

The hair care composition described herein can contain a film forming polymer that is soluble and/or dispersible in water or alcohol. Such film forming polymers can have a molecular weight from about 100 Daltons to about 2,500,000 Daltons (e.g., from about 500 Daltons to about 2,000,000 Daltons or from about 1,000 Daltons to about 1,000,000 Daltons).

The hair care compositions described herein can contain any amount of a film forming polymer. For example, a hair care composition can contain an effective amount of a film forming polymer such that the hair care composition provides shape retention, substantivity, thermal protection, and chemical dye protection. Typically, from about 0.001 percent to about 10 percent (e.g., from about 0.01 percent to about 8 percent or from about 0.05 percent to about 6 percent), by weight, of the hair care composition is a film forming polymer.

Any method can be used to obtain a film forming polymer. For example, a film forming polymer can be obtained from BASF (Mount Olive, N.J.), National Starch Chemicals (Bridgewater, N.J.), ISP (Wayne, N.J.), or PPG Industries, Inc. (Pittsburgh, Pa.).

Silicone and Silicone Derivatives

The hair care compositions of the invention can contain one or more silicone or silicone derivative. A silicone or silicone derivative can be used to lubricate hair. Silicon and silicone derivative also can be used as plasticizer. Examples of silicon and silicone derivatives include, without limitation, non-volatile silicone fluids such as dimethicone copolyol, polydimethylsiloxane, cyclic dimethyl polysiloxane, aminosilicones, and phenylsilicones. Other examples include, without limitation, cyclopentasiloxane, dimethicone copolyol, cetyl dimethicone, cetyl dimethiconecopolyol, and aminopropyl PEG-7 PEG-3 dimethicone copolyol.

The hair care compositions described herein can contain any amount of a silicone or silicone derivative. For example, a hair care composition can contain an effective amount of silicone or silicone derivative such that the hair care composition provides lubrication to the hair. Typically, from about 0.001 percent to about 10 percent (e.g., from about 0.01 percent to about 4 percent or from about 0.05 percent to about 2.5 percent), by weight, of the hair care composition is silicone or a silicone derivative. Typically, the hair care compositions of the invention contain silicone or a silicone derivative having a viscosity from about 50 centistokes (cst) to about 2,000,000 cst (e.g., from about 100 cst to about 1,500,000 cst or from about 150 cst to about 1,000,000 cst) at 25° C.

Any method can be used to obtain silicone or a silicone derivative. For example, silicone or a silicone derivative can be obtained from Goldschmidt (Hopewell, Va.), GE (Waterford, N.Y.), or Dow Corning (Auburn, Mich.).

Chelators and Dispersants

The hair care compositions described herein can contain one or more chelator and/or one or more dispersant. A chelator can be used to bind transition metals or other metals that act as catalysts for auto-oxidation. A dispersant also can be used to provide binding to transition metals. Examples of chelators include, without limitation, citric acid, citric acid soluble salts, phosphates, nitrilotriacetic acid, soluble salts of nitrilotriacetic acid, sodium carboxymethyl oxymalonate, sodium carboxymethyl oxysuccinate, ethylendiaminetetracarboxylic acid, soluble salts of ethylendiaminetetracarboxylic acid, and polymers and copolymers of acrylic acid, methacrylic acid, and maleic acid. Examples of dispersants (e.g., organic dispersants) include, without limitation, soluble salts of low molecular weight homopolymers or copolymers of polyacrylic acids, partially hydrolyzed polyacrylamides, maleic anhydride copolymers, and polyaspartic acid. For example, a hair care composition can contain a soluble salt of low molecular weight acrylic acid polymers.

The hair care compositions described herein can contain any amount of a chelator or a dispersant. Typically, from about 0.001 percent to about 5 percent (e.g., from about 0.01 percent to about 4 percent or from about 0.05 percent to about 2.5 percent), by weight, of the hair care composition is a chelator. In addition, from about 0.001 percent to about 5 percent (e.g., from about 0.01 percent to about 4 percent or from about 0.05 percent to about 2.5 percent), by weight, of the hair care composition is a dispersant.

Thickeners

The hair care compositions described herein can contain one or more thickeners. A thickener can be a crosslinked polycarboxylate polymer such as a carboxyvinyl polymer. For example, a styling gel, conditioner, or shampoo described herein can contain a carboxyvinyl polymer thickener. Various thickeners are described in U.S. Pat. No. 2,798,053. Any method can be used to obtain a thickener. For example, a thickener can be obtained from B. F. Goodrich Company (New York, N.Y.) under the trade name Carbopol. Another thickener can be crosslinked polycarboxylate polymers marketed under the tradename Polygel by 3V (Weehawken, N.J.). A thickener also can be xanthan gum or a cellulose analog. Xanthan gum is a biopolysaccharide obtained from the growth of Xanthomonas spp. Suitable xanthan gums include, without limitation, products such as Keltrol and Kelzan obtained from Kelco Corporation (San Diego, Calif.) as well as products such as Rhodipol and Rhodigel obtained from Rhodia (Cranberry, N.J.). Cellulose analogs include, without limitation, hydroxypropylcellulose and hydroxyethylcellulose.

When a crosslinked polycarboxylate polymer such as Carbopol 940 is used as a thickener, a weak acid can be dissolved in water prior to dispersing the thickener in order to retard hydration of the thickener. For example, citric acid can be dissolved in water, and the thickener can be dispersed. After dispersing the thickener, a pH adjusting agent can be added followed by the remaining ingredients including optional ingredients such as hair fixatives, surfactants, conditioning agents, vitamins, preservatives, fragrances, and colorants.

In some cases, the ratio of a thixotropic thickener to water can be high. In such cases, the thixotropic thickener can be preblended with a non-aqueous ingredient prior to addition. For example, the thixotropic thickener can be dry blended with a solid ingredient or dispersed in a non-aqueous liquid ingredient prior to addition. It is noted that other process variations may be employed to prepare the compositions described herein. It also is noted that the final pH can be adjusted to a value between 4.0 and 8.5 measured as is.

Surfactants

The hair care compositions described herein can contain one or more surfactants. A surfactant can be an anionic, cationic, amphoteric, zwitterionic, or nonionic surfactant. Examples of anionic surfactants that can be used include, without limitation, alkylsulfate, alkylolefin sulfonate, alkyl ether sulfate, alkylarylsulfonates, alkylsuccinate, alkyl sulphosuccinates, acyl taurates, acyl glutamates, N-alkyl sarcosinates, alkylphosphate, alkyl ether phosphates, and alkyl ether carboxylates as well as sodium, potassium, magnesium, ammonium alkanolamine, and alkylamine salts thereof. Alkyl and acyl groups generally contain from 8 to 20 carbon atoms and can be unsaturated. Alkyl ether sulfates, alkyl ether phosphates, and alkyl ether carboxylates can contain from one to about 10 ethylene oxide and/or propylene oxide units per molecule (e.g., about 2 to about 5 ethylene oxide units per molecule). Other examples of anionic surfactants include, without limitation, sodium oleyl sulfates, ammonium lauryl sulfonate, sodium lauryl sulfate, ammonium lauryl sulfates, sodium cocoyl sulfates, sodium octylsulfosuccinate, ammonium lauryl sulfosuccinate, sodium lauryl sarcosinate, and sodium alpha-olefin sulfonates. For example, anionic surfactants such as ammonium or sodium lauryl ether sulfates with 1 EO, 2 EO, or 3 EO, ammonium or sodium salts of lauryl sulfates and/or ammonium or sodium cocoglucose sulfosuccinate can be used to provide a clean lather feel in shampoos. Additional anionic surfactants that can be used can be found in McCutcheon's Emulsifiers and Detergents (1999 North American Edition).

Nonionic surfactants that can be used include, without limitation, alkyl ethoxylates such as those that are formed by condensing one mole of a saturated or unsaturated, straight or branched chain fatty alcohol or fatty acid containing about 10 to about 20 carbon atoms chain length with from about 4 moles to about 40 moles of ethylene oxide or propyleneoxide, alkyl polyglycosides, and alkylalkanolamides. Other examples include laurylamido DEA, palmitamide MEA, cocamide MEA, coco monoisopropanolamide, glycolstearate, stearyamidopropyl dimethylamine, glycoldistearate, polyoxyethylene sorbitan monolaurate and monostearates, cetyl alcohol, stearyl alcohol, ceterath-20, and alkylpolyglucoside. Additional nonionic surfactants that can be used can be found in McCutcheon's Emulsifiers and Detergents (1999 North American Edition).

Examples of amphoteric surfactants and zwitterionic surfactants that can be used include, without limitation, alkyl amineoxide (e.g., laurylamine oxide), alkyl betaines (e.g., cocamidopopyl betaine), alkylamidopropylbetaines, alkylsulfobetaines (e.g., cocodimethyl sulphopropylbetaine), alkylglycinates, alkycarboxyglycinates, alkylamphopropionates (e.g., cocoamphoprioionate), alkylamphoglycinates, alkylamidohydroxysultaines, alkyl amphoacetates, and alkyl amphodiacetates.

Examples of cationic surfactants that can be used include, without limitation, quaternary ammonium salts, ricinoelamidopropyl ethyldimonium ethosulfate, isostearmidopropyl ethylimidonium ethosulfate, lineoleamidopropyl PG-diminium chloride phosphate, cinnamidoproyltrimethyl ammonium chloride, behentrimmonium methosulfate, and lanolinamidopropyldimonium ethosulfate. Additional cationic surfactants that can be used can be found in McCutcheon's Emulsifiers and Detergents (1999 North American Edition).

Cationic Conditioning Polymers

The hair care compositions described herein can contain one or more cationic conditioning polymers. Cationic conditioning polymer can be used to provide shape retention, increased substantivity, and thermal or chemical dye protection. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

The cationic conditioning polymer used can have a glass transition temperature from about −20° C. to about 150° C. (e.g., from about −10° C. to about 100° C. or from about 0° C. to about 80° C.). In addition, a hair care composition can contain a cationic conditioning polymer that is soluble and/or dispersible in water or alcohol. Such cationic conditioning polymers can have a molecular weight from about 100 Daltons to about 2,500,000 Daltons (e.g., from about 500 Daltons to about 2,000,000 Daltons or from about 1,000 Daltons to about 1,000,000 Daltons).

The hair care compositions described herein can contain any amount of a cationic conditioning polymer. For example, a hair care composition can contain an effective amount of a cationic conditioning polymer such that the hair care composition provides shape retention, substantivity, thermal protection, and chemical dye protection. Typically, from about 0.001 percent to about 10 percent (e.g., from about 0.01 percent to about 8 percent or from about 0.05 percent to about 6 percent), by weight, of the hair care composition is a cationic conditioning polymer.

Vitamins

The hair care compositions described herein can contain one or more vitamins such as provitamin B (e.g., panthenol, phytantriol, or ethylpanthenol), Vitamin A acetate, Vitamin A palmitate, Vitamin D, Vitamin E, Vitamin A, tocophryl acetate, and tocophryl palmitate, and/or mixtures thereof.

Botanical Extracts

The hair care compositions described herein can contain one or more herbal extract such as standardized herbal extracts that are dispersible and/or soluble in aqueous medium. Examples of herbal extracts that can be used include, without limitation, chamomile, rosemary, aloe, nettle, centella asiatica, ginkgo biloba, and witch hazel. Typically, the herbal extract is delivered in a carrier such as water, propylene glycol, hydroalcoholic, glycerine, or butylene glycol.

Other Ingredients

The hair care compositions described herein can contain one or more optional ingredients such as hydrotropes, preservatives, botanical oil, fragrances, colorants, pH adjusting ingredients, and the like.

pH Adjustment

The final pH of the undiluted product should be between 4.0 and 8.5. To obtain such a final pH, the pH of the composition can be adjusted. A pH-adjusting agent can be used to adjust the pH. It will be appreciated that the pH adjustment can be accomplished with any of a wide variety of acids should the composition have a pH too high (e.g., greater than 8.5 before adjustment). Likewise, it will be appreciated that the pH adjustment can be accomplished with any of a wide variety of bases should the composition have a pH too low (e.g., greater than 4.0 before adjustment). Shampoos, conditioners, and styling aids were found to have improved stability when the pH is between pH 4.0 to 8.5. In addition, hair care compositions having a pH within this range are aesthetically-pleasing and compatible with skin or hair.

Methods of Treating Hair

The compositions provided herein can be used to treat hair such that hair damage is reduced. Specifically, the invention provides a method that involves (1) applying a hair care composition containing a macrocyclic lactone and/or eicosanoate ester, and (2) heating the hair so that the macrocyclic lactone and/or eicosanoate ester reacts with the hair. Typically, the hair is heated to at least about 75° C. (e.g., at least about 80° C. or 85° C.). For example, the hair can be heated to a temperature from about 75° C. to about 150° C. Any method can be used to heat hair. For example, steam, hot oil, a hot iron, or a blow dryer can be used to heat hair. When using hot gas, the gas can contain at least about 1 percent of steam, by volume. In addition to steam, the gas can contain solvent vapor and/or vaporized compounds as well as gasses such as oxygen or nitrogen and/or gas mixtures such as air.

Heating hair exposed to a hair care composition containing a macrocylic lactone and/or an eicosanoate ester can allow those molecules to react with hair forming a covalent amide bond. In addition, the repeated accumulative effect of applying such hair care compositions with heat can create hydroxyfatty amides or fatty amides with hair protein, thus providing long-term lubrication and conditioning. Thus, the methods described herein can be used to generate a greater quantity of amide bound to hair. In fact, the quantity of amides remaining on hair after rinsing or shampooing is greater when heat is used as opposed to when heat is not used.

After briefly heating the treated hair, the hair is cooled. The hair can be cooled rapidly by, for example, subjecting the hair to a flow of air having an ambient temperature (e.g., about 23° C.). Alternatively, the hair can be cooled by allowing it to stand at room temperature.

If desired, an apparatus can be used to heat the hair. For example, the devices described in French Patent Application FR-A-2 273 492 can be used to heat hair. Typically, a device is used that can uniformly and homogeneously (1) heat the hair fibers without overheating and (2) cool the hair fibers after being heated.

The invention will be further described in the following examples, which do not limit the scope of the invention described in the claims.

EXAMPLES

Example 1

Shampoo Composition

A shampoo composition was prepared by mixing the following ingredients. The amount of each ingredient is provided as percent by weight.

| Ingredient | W/W % |
| --- | --- |
| Water | Q.S. to 100.00 |
| Tetrasodium EDTA | 0.15 |
| Citric Acid | 0.05 |
| Glycol Stearate | 0.9 |
| Ammonium Laureth Sulfate | 25.2 |
| Cocamide MEA | 1.00 |
| Ammonium Lauryl Sulfate | 22.5 |
| Cocamidopropyl Betaine | 9.9 |
| Isostearamidopropyl Morpholine Lactate | 0.5 |
| DL-Panthenol | 0.100 |
| Phytantriol | 0.05 |
| Tocopheryl Acetate (Vitamin E Acetate) | 0.5 |
| Cinnamidopropyl Trimethyl Ammonium Chloride | 0.5 |
| PVP/DMAPA Acrylates Copolymer | 3.00 |
| Wheat Germ Protein | 0.03 |
| Cocodimonium Hydroxypropyl Hyrdroylzed Wheat Protein | 0.05 |
| Cyclopentasiloxane | 0.05 |
| Methyl 11-cis eicosenoate | 0.5 |
| Hexadecanolide | 0.5 |
| Polyquaternium 7 (Mackernium 007) | 8.00 |
| Preservative | 0.8 |
| Fragrance | 1.5 |

Example 2

Styling Gel Composition

A styling gel composition was prepared by mixing the following ingredients. The amount of each ingredient is provided as percent by weight.

| Ingredient | W/W % |
| --- | --- |
| Water | Q.S. to 100 |
| Tetrasodium EDTA | 0.005 |
| Carbapol (Carbomer 940) | 0.3 |
| AMP-95 | 0.39 |
| Benzophenone-4 | 0.01 |
| PVP K90 | 2.7 |
| PVP/Acrylates/Lauryl Methacrylate Copolymer | 1.5 |
| Triethyl Citrate | 0.3 |
| Methyl 11-cis eicosenoate | 0.5 |
| Hexadecanolide | 0.2 |
| Dimethicone Copolyol (DC-190) | 0.02 |
| D-Panthenol | 0.02 |
| Fragrance | 0.1 |
| Preservative | 0.08 |

Example 3

Styling Hair Spray Composition

A styling hair spray composition was prepared by mixing the following ingredients. The amount of each ingredient is provided as percent by weight.

Example 4

Hair Conditioning Composition

A hair conditioning composition was prepared by mixing the following ingredients. The amount of each ingredient is provided as percent by weight.

| Ingredient | W/W % |
| --- | --- |
| Water | Q.S. to 100 |
| SD Alcohol 23 A | 55 |
| AMP-95 | 0.4 |
| Benzophenone-4 | 0.03 |
| Sodium Benztriazolyl Butylphenol Sulfonate | 0.03 |
| VA/Crotonates/Vinyl Neodecanoate Copolymer (Resyn 28-2930) | 3.25 |
| Octylacrylamide/Acrylates/Butylaminoethyl Methacrylate Copolymer (Amphomer 28-4910) | 1.25 |
| Dimethicone Copolyol (Dow Corning 190 Surfactant) | 0.05 |
| Methyl 11-cis eicosenoate | 0.05 |
| Hexadecanolide | 0.05 |
| Triethyl Citrate (Citroflex 2) | 0.3 |
| Phytantriol | 0.05 |
| DL-Panthenol (50% Liquid) | 0.05 |
| Tocopheryl Acetate (Vitamin E Acetate) | 0.05 |
| Cocamidopropyl Betaine | 0.1 |
| Cinnamidopropyltrimonium Chloride | 0.05 |
| Fragrance | 0.7 |

Example 5

Hair Conditioning Composition

A hair conditioning composition was prepared by mixing the following ingredients. The amount of each ingredient is provided as percent by weight.

| Ingredient | W/W % |
| --- | --- |
| Water | Q.S. to 100 |
| Hydroxypropylmethylcellulose | 0.3 |
| Tetrasodium EDTA | 0.05 |
| Citric Acid | 0.1 |
| Cetearyl Alcohol (and) Ceteareth-20 | 0.75 |
| Stearamidopropyl Dimethylamine (Mackine 301 from McIntyre) | 1 |
| Stearic Acid | 0.5 |
| Cetyl Alcohol | 1.1 |
| Stearyl Alcohol | 0.75 |
| Cyclomethicone (SF1202~GE) | 1.8 |
| Dimethicone Copolyol (Abil B 8832) | 0.5 |
| Behentrimonium Methosulfate, | 2.4 |
| Lanolinamidopropyldimonium Ethosulfate, Cetearyl Alcohol | |
| Wheat Gerrn Protein, and Water (Dragoderm) | 0.25 |
| Cocodimonium Hydroxypropyl Hydrolyzed Wheat Protein | 0.25 |
| DL Panthenol | 0.1 |
| Phytantriol | 0.1 |
| Tocopheryl Acetate (Vitamin E Acetate) | 0.05 |
| Cinnamidopropyl Trimethyl Ammonium Chloride | 0.05 |
| PVP/DMAPA Acrylates Copolymer | 1.5 |
| Hydroxypropyltrimonium Honey | 0.05 |
| Methyl 11-cis eicosenoate | 0.2 |
| Hexadecanolide | 0.05 |
| Polyquaternium 7 (Mackernium 007) | 4 |
| Fragrance | 0.95 |
| Preservative | 0.08 |

| Ingredient | W/W % |
| --- | --- |
| Water | Q.S. to 100 |
| Hydroxypropylmethylcellulose | 0.3 |
| Tetrasodium EDTA | 0.05 |
| Citric Acid | 0.1 |
| Cetearyl Alcohol (and) Ceteareth-20 | 0.75 |
| Stearamidopropyl Dimethylamine (Mackine 301 from McIntyre) | 1 |
| Stearic Acid | 0.5 |
| Cetyl Alcohol | 1.1 |
| Stearyl Alcohol | 0.75 |
| Cyclomethicone (SF1202~GE) | 1.8 |
| Dimethicone Copolyol (Abil B 8832) | 0.5 |
| Behentrimonium Methosulfate, | 2.4 |
| Lanolinamidopropyidimonium Ethosulfate, Cetearyl Alcohol | |
| Wheat Germ Protein, and Water (Dragoderm) | 0.25 |
| Cocodimonium Hydroxypropyl Hydrolyzed Wheat Protein | 0.25 |
| DL Panthenol | 0.1 |
| Phytantriol | 0.1 |
| Tocopheryl Acetate (Vitamin E Acetate) | 0.05 |
| Cinnamidopropyl Trimethyl Ammonium Chloride | 0.05 |
| PVP/DMAPA Acrylates Copolymer | 1.5 |
| Hydroxypropyltrimonium Honey | 0.05 |
| Methyl 11-cis eicosenoate | 0.2 |
| Hexadecanolide | 0.05 |
| Polyquaternium 7 (Mackernium 007) | 4 |
| Fragrance | 0.95 |
| Preservative | 0.08 |
| Grape skin extract | 0.1 |
| Benzophenone | 0.1 |
| Benzotriazole | 0.1 |

Example 6

Non-aerosol Mousse Composition

A non-aerosol mousse composition was prepared by mixing the following ingredients. The amount of each ingredient is provided as percent by weight.

| Ingredient | W/W % |
| --- | --- |
| Water | Q.S. To 100 |
| Polyquaternium 11 | 3.0 |
| PVP (PVP K-90) | 1.0 |
| PVP (PVP K-30) | 0.5 |
| Cocamidopropyl Betaine | 3.0 |
| PVP/VA Copolymer (PVP/VA E735) | 3.0 |
| Polysorbate 20 | 1.0 |
| Tocopheryl Acetate (Vitamin E Acetate) | 0.5 |
| Phytantriol | 0.5 |
| DL-Panthenol | 0.1 |
| Cinnamidopropyl Trimonium Chloride | 0.05 |
| Quatermized Wheat Protein | 0.2 |
| Dimethiconecopolyol | 0.05 |
| Methyl 11-cis eicosenoate | 0.05 |
| Hexadecanolide | 0.05 |
| Fragrance | 0.7 |
| Preservative | 0.076 |

Example 7

Analysis of Shampoo Compositions

Three shampoo compositions were applied to tress samples and evaluated. Briefly, human hair tresses about one inch wide and six inches long weighing about 5 grams were wet with tap water at about 30° C. About two grams of the shampoo composition to be tested was spread throughout the tress. Once applied, a lather was worked up with fingers. After rinsing in warm tap water, another two grams of shampoo was applied, lathered, and rinsed. After the second rinsing, the excess water was removed from each tress sample by towel drying.

Once the excess water was removed, each tress sample was evaluated by combing the wet tress sample with a 4 ½ inch×1 inch Goody comb. After this wet combing test, each tress sample was dried using a Conair Supreme™ (Model 1500) hair dryer on high setting and evaluated for combing ease and static build-up by combing (dry combing test). Wet combing and dry combing observations were conducted to evaluate combing ease, which is the ease of aligning fibers of an assembly with a comb so they are essentially parallel (C. R. Robbins, Chemical and Physical Behavior of Human Hair, 3rd Ed. Springer-Verlag 1994). Curvature, friction, stiffness, diameter or cross-sectional area, length, and cohesion are all relevant to combing ease. For the wet and dry combing tests, each tress sample received a score from one to five with a five being the best.

The three shampoo compositions tested were as follows. Shampoo composition number one did not contain hexadecanolide or eicosanoate (Sample #1 in Table 1). Shampoo composition number two contained polyquaternium and silicone (Sample #2 in Table 1). Shampoo composition number three contained 0.5 percent hexadecanolide and 0.5 percent eicosanoate (Sample #3 in Table 1).

Example 8

Analysis of Conditioner Compositions

Seven conditioner compositions were applied to tress samples and evaluated. Briefly, previously shampooed human hair tresses about one inch wide and six inches long weighing about 5 grams were wet with tap water at about 30° C. After blotting the tress samples to remove the excess water, about two grams of the conditioner composition to be tested was worked into the tress. After rinsing in warm tap water and removing the excess water by towel blotting, each tress sample was evaluated using the wet and dry combing tests described in Example 7.

The seven conditioner compositions tested were as follows. Conditioner composition number one contained 0.5 percent hexadecanolide, 0.5 percent methyl eicosanoate, silicone, and cationic polymer (Sample #1 in Table 2). Conditioner composition number two did not contain hexadecanolide or eicosanoate (Sample #2 in Table 2). Conditioner composition number three did not contain hexadecanolide, eicosanoate, silicone, or cationic polymer (Sample #3 in Table 2). Conditioner composition number four contained polyquaternium (Sample #4 in Table 2). Conditioner composition number five contained 0.5 percent

TABLE 1

| Sample # | Wet Comb Rating | Dry Comb Rating | Comments |
|---|---|---|---|
| 1 | 3 | 2 | Foam was rich and creamy. The foam increased the second time. The product rinsed out well. The tress felt somewhat soft and silky when wet and dry. Some static was noticed. |
| 2 | 3 | 3 | Foam had lots of volume but felt light. The foam was not dense or tight (loose). The foam was the same amount the second time. The product rinsed out well. The tress felt somewhat squeaky when dry. There was significant static. |
| 3 | 5 | 5 | Foam was rich and creamy (dense and thick). The foam was the same amount the second time. The product rinsed out well. The tress felt very soft and silky when wet and dry. No static was noticed. |

These results indicate that hair treated with shampoo compositions containing hexadecanolide and eicosanoate have better combing characteristics than hair treated with shampoo compositions lacking hexadecanolide and eicosanoate.

hexadecanolide and 0.5 percent methyl eicosanoate (Sample #5 in Table 2). Conditioner composition number six contained silicones and polyquaternium (Sample #6 in Table 2). Conditioner composition number seven contained silicone (Sample #7 in Table 2).

TABLE 2

| Sample # | Wet Comb Rating | Dry Comb Rating | Comments |
|---|---|---|---|
| 1 | 5 | 5 | Rinsed well (applied well); when dry the feel was very soft; no static noticed. It looked very lustrous. |
| 2 | 4 | 3 | Rinsed well (applied well); felt dry after rinse; felt slight soft; no static noticed; slight luster. |
| 3 | 2 | 2 | Rinsed well; felt dry after rinse; when dry the feel was not soft; no static noticed, no luster. |
| 4 | 3 | 1 | Rinsed well; felt dry after rinse; felt dry when wet and dry; lots of static was noted, no luster. |
| 5 | 5 | 4 | Rinsed well (applied well); felt slightly dry afier rinse; when dry felt silky and soft, no static noticed; very good luster |
| 6 | 3 | 3 | Rinsed well; felt dry after rinse; when dry felt silky and soft; no static noticed, slight luster. |

TABLE 2-continued

| Sample # | Wet Comb Rating | Dry Comb Rating | Comments |
|---|---|---|---|
| 7 | 4 | 3 | Rinsed well; felt dry after rinse; when dry felt soft; no static noticed, slight luster. |

These results indicate that hair treated with conditioner compositions containing hexadecanolide and eicosanoate have better combing characteristics than hair treated with conditioner compositions lacking hexadecanolide and eicosanoate.

Example 9

Aesthetic Assessment of Conditioning Compositions

The conditioning composition described in Example 4 and a leading salon brand conditioner were packaged separately in unlabeled bottles. The unlabeled bottles were placed with respondents in Knoxville, Tenn. and Idaho Falls, Id. in a monadic sequential test. The order of presentation was randomized. Respondents were asked to use each product for a week prior to completing and returning a self-administered questionnaire. The self-assessment was based on a 9-scale rating system with the higher number indicating a better score. Over 100 respondents from Knoxville, Tenn. and Idaho Falls, Id. participated in the test. The data was collected, proofed, and analyzed statistically using a student's t-test (Table 3). Sample number 1 refers to the conditioner composition described in Example 4 while sample number 2 refers to the leading salon brand conditioner.

TABLE 3

| Sample # | Rinse-ability | Combing | Silky | Manage-ability | Body | Overall Preference |
|---|---|---|---|---|---|---|
| 1 | 6.182 | 5.761 | 5.716 | 6.030 | 5.642 | 5.731 |
| 2 | 5.414 | 5.214 | 4.543 | 4.972 | 4.634 | 4.352 |
| t-test | 0.039 | 0.200 | 0.004 | 0.007 | 0.005 | 0.001 |

These results indicate that the conditioner compositions of the invention are more preferable than a leading salon conditioner.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An aqueous hair care composition comprising a macrocyclic lactone and an eicosanoate ester, wherein said macrocyclic lactone is, by weight, from about 0.01 percent to about 5.0 percent of said composition, and wherein said eicosanoate ester is, by weight, from about 0.01 percent to about 8.0 percent of said composition.

2. The composition of claim 1, wherein said composition is a shampoo, conditioner, styling gel, styling spray, or styling non-aerosol mousse.

3. The composition of claim 1, wherein said macrocyclic lactone is hexadecanolide.

4. The composition of claim 1, wherein said eicosanoate ester is a branched eicosanoate ester.

5. The composition of claim 1, wherein said eicosanoate ester is a straight eicosanoate ester.

6. The composition of claim 1, wherein said eicosanoate ester is methyl 11-cis eicosenaote, 18-methyl eicosanaote, or a quaternary ester of 18-methyl eicosanaote.

7. The composition of claim 1, wherein said composition further comprises a conditioning polymer.

8. The composition of claim 7, wherein said conditioning polymer is a cationic conditioning polymer.

9. The composition of claim 7, wherein said conditioning polymer is, by weight, from about 0.001 percent to about 10.0 percent of said composition.

10. The composition of claim 1, wherein said composition further comprises silicone.

11. The composition of claim 10, wherein said silicone is, by weight, from about 0.001 percent to about 10.0 percent of said composition.

12. The composition of claim 10, wherein said silicone is, by weight, from about 0.05 percent to about 2.5 percent of said composition.

13. The composition of claim 10, wherein the viscosity of said silicone is from about 50 cst to about 2,000,000 cst at 25° C.

14. The composition of claim 10, wherein the viscosity of said silicone is from about 150 cst to about 1,000,000 cst at 25° C.

15. The composition of claim 1, wherein said composition further comprises a surfactant.

16. The composition of claim 15, wherein said surfactant is, by weight, from about 0.001 percent to about 10.0 percent of said composition.

17. The composition of claim 15, wherein said surfactant is an anionic surfactant.

18. The composition of claim 15, wherein said surfactant is a cationic or nonionic surfactant.

19. The composition of claim 1, wherein said composition comprises a thickener.

20. The composition of claim 1, wherein the pH of said composition is from about 4.0 to about 8.5.

21. The composition of claim 1, wherein said composition further comprises a conditioning polymer and silicone.

22. The composition of claim 1, wherein said composition further comprises:
   a) a conditioning polymer, said conditioning polymer being from about 0.001 percent to about 10.0 percent of said composition; and
   b) silicone, said silicone being from about 0.001 percent to about 10.0 percent of said composition.

23. A method of treating hair, said method comprising applying a composition to said hair, said composition comprising a macrocyclic lactone and an eicosanoate ester, wherein said macrocyclic lactone is, by weight, from about 0.01 percent to about 5.0 percent of said composition, and wherein said eicosanoate ester is, by weight, from about 0.01 percent to about 8.0 percent of said composition.

24. A method of treating hair, said method comprising (a) applying a composition to said hair, said composition comprising a macrocyclic lactone and an eicosanoate ester, wherein said macrocyclic lactone is, by weight, from about 0.01 percent to about 5.0 percent of said composition, and wherein said eicosanoate ester is, by weight, from about 0.01 percent to about 8.0 percent of said composition; and (b) heating said hair to at least 75° C.

* * * * *